United States Patent
Kamiya et al.

(10) Patent No.: US 7,354,617 B2
(45) Date of Patent: Apr. 8, 2008

(54) FIXING BELT AND METHOD FOR EVALUATING IT

(75) Inventors: Kohji Kamiya, Ohta-ku (JP); Kyoichi Ashikawa, Ohta-ku (JP); Norihiko Aze, Ohta-ku (JP); Minoru Matsuo, Ohta-ku (JP); Nozomu Takahata, Ohta-ku (JP)

(73) Assignee: Ricoh Company, Ltd., Tokyo (JP)

( * ) Notice: Subject to any disclaimer, the term of this patent is extended or adjusted under 35 U.S.C. 154(b) by 471 days.

(21) Appl. No.: 11/034,828

(22) Filed: Jan. 14, 2005

(65) Prior Publication Data

US 2005/0123673 A1    Jun. 9, 2005

Related U.S. Application Data

(62) Division of application No. 10/322,525, filed on Dec. 19, 2002, now Pat. No. 6,861,124.

(30) Foreign Application Priority Data

Dec. 19, 2001   (JP)   ............... 2001-385377
Aug. 29, 2002   (JP)   ............... 2002-250229

(51) Int. Cl.
*C23C 16/52*   (2006.01)
*B23Q 17/20*   (2006.01)
(52) U.S. Cl. ............. 427/8; 427/535; 427/551; 427/553; 427/248.1; 204/192.1; 73/78; 73/81
(58) Field of Classification Search .......... 427/8, 427/535, 551, 553, 248.1; 204/192.1; 73/78; 73/81
See application file for complete search history.

(56) References Cited

U.S. PATENT DOCUMENTS

| | | | | |
|---|---|---|---|---|
| 4,671,104 | A | * | 6/1987 | Fischer .......................... 73/81 |
| 4,699,000 | A | * | 10/1987 | Lashmore et al. ............. 73/81 |
| 5,724,638 | A | | 3/1998 | Isogai et al. |
| 5,765,086 | A | | 6/1998 | Kishino et al. |
| 6,263,172 | B1 | * | 7/2001 | Suzuki et al. ................. 399/67 |
| 6,618,573 | B2 | | 9/2003 | Ishikawa et al. |
| 6,647,238 | B2 | | 11/2003 | Takagi et al. |

(Continued)

FOREIGN PATENT DOCUMENTS

JP    64-90477    4/1989

(Continued)

*Primary Examiner*—Bret Chen
(74) *Attorney, Agent, or Firm*—Oblon, Spivak, McClelland, Maier & Neustadt, P.C.

(57) ABSTRACT

A method for evaluating a fixing belt includes forming a fixing belt which includes a substrate, an elastic layer laminated on the substrate, and a mold releasing layer laminated on the elastic layer. A universal hardness test for the fixing belt is performed. The fixing belt is judged as an acceptable product if a creep value $C_{HU}$ is included within a range of $0.40 \leq C_{HU} \leq 3.50$ (%) when the universal hardness test is performed for the fixing belt and when the creep value $C_{HU}$, which is measured from the side of the mold releasing layer, is defined by the following formula:

$$C_{HU} = (h_2 - h_1)/h_1 \times 100 \ (\%)$$

where $h_1$ is a pushed depth when a test load reaches a predetermined value which is kept for a predetermined period of time, and $h_2$ is a pushed depth when a predetermined period of time is elapsed after the test load is removed.

4 Claims, 10 Drawing Sheets

U.S. PATENT DOCUMENTS

2002/0118982 A1 * 8/2002 Fuma .................. 399/329

FOREIGN PATENT DOCUMENTS

| | | |
|---|---|---|
| JP | 2-309377 | 12/1990 |
| JP | 4-76587 | 3/1992 |
| JP | 5-19651 | 1/1993 |
| JP | 6-8964 | 2/1994 |
| JP | 6-318001 | 11/1994 |
| JP | 9-44014 | 2/1997 |
| JP | 10-198201 | 7/1998 |
| JP | 10-274894 | 10/1998 |
| JP | 11-184291 | 7/1999 |
| JP | 2001-282033 | 10/2001 |
| JP | 2001-312170 | 11/2001 |

* cited by examiner

FIXING BELT AND METHOD FOR EVALUATING IT

BACKGROUND OF THE INVENTION

1. Field of the Invention

The present invention relates to a fixing belt which is utilized in an electro-photographic apparatus and the like and to a method for evaluating the fixing belt.

2. Description of the Prior Art

In general, there is an electro-photographic apparatus and the like in which a belt fixing device having a fixing belt utilized is equipped.

As one example, such a belt-fixing device is disclosed in Japanese Patent Laid-Open Publication No. Hei 06-318001. The belt-fixing device disclosed in the publication is constituted so that it includes a fixing roller and a heating roller, and an endless like fixing belt having on a surface thereof a mold releasing layer is loaded between the both rollers, a pressure roller is disposed under the fixing roller to pinch the fixing belt to pass a paper through a nipping portion between the fixing belt and the nip roller.

Further, the belt-fixing device is provided with a preheating process which is arranged between the heating roller and the nipping portion to preheat toner beforehand.

However in the prior art belt fixing device, because the fixing roller is made of solid rubber, it is not possible to absorb a stress caused by thickness of the paper, a pressure distribution in the nipping portion is in an uneven state such that the pressure is low around an entrance and an exit of the nipping portion and is most high at a center part of the nipping portion. On the other hand, because water included in the paper is evaporated with heat brought by the fixing belt while the paper is brought through the preheating process, there is a high possibility that partial convenes and concaves are generated on the paper. When the paper having such convenes and concaves passes through the nipping portion having such uneven pressure distribution, a portion where the paper is partially restrained strongly is generated to further exaggerate the convenes and concaves thereby occurring crumples on the paper.

To prevent an occurrence of such crumples on the paper, for example, in Japanese Patent Laid-Open Publication No. Hei 10-274894 there is disclosed a method that a circumferential speed ratio between the fixing roller and the nip roller is set in a range of 0.97-1.03 and a delay of the nip roller is inhibited in order to reduce a stress suffering on the paper and thereby the occurrence of crumples on the paper are prevented.

Also, for example, in Japanese Patent Laid-Open Publication No. Hei 7-92840 there is disclosed a method that a covering layer of fluorine containing resin is arranged on an elastic layer on a conductive axis body of the fixing roller and the nip roller to prevent an occurrence of the crumples on the material paper.

Further, in Japanese Patent Laid-Open Publication No. 2001-282033 there is disclosed a method that temperature around edge sides of a paper passing part in the nipping portion along axial direction of the fixing roller and the nip roller are set higher than that of central part side to prevent an occurrence of the crumples on paper.

It is important that a surface of the fixing belt has an appropriate flexibility in order to prevent the occurrence of crumples of this kind.

However, any one of the above described prior arts is not based on flexibility of the surface of fixing belt, and there has no method for evaluating flexibility of surface of the fixing belt, so that only a visual examination and so on has been carried out with respect to the fixing belts delivered from the manufacturer of parts.

In this way, because there is no method for evaluating about whether or not the fixing belt has appropriate flexibility at its surface in the prior art, all the fixing belts which pass the visual examination and so on, are adapted to be utilized on the belt-fixing device. As a result, when in a case a fixing belt that has not appropriate flexibility at its surface, comes to be mixed in the delivered lot, crumple is generated on the paper and thereby it causes degradation in quality level though several kinds of countermeasures are introduced and achieved.

SUMMARY OF THE INVENTION

It is therefore an object of the present invention to provide a fixing belt and a method for evaluating it in which the fixing belt is accurately evaluated whether or not it has appropriate flexibility at its surface and thereby an occurrence of crumple on a paper can be prevented.

To accomplish the aforementioned object, according to the present invention there is provided a fixing belt comprising: a substrate; an elastic layer which is laminated on the substrate; and a mold releasing layer which is laminated on the elastic layer, wherein a flexibility of the fixing belt on its surface is determined by a creep value of the fixing belt measured from the side of the mold releasing layer.

More specifically, the fixing belt is judged as an acceptable product if a creep value $C_{HU}$ is included within a range of $0.40 \leq C_{HU} \leq 3.50$ (%) when a universal hardness test is achieved for the fixing belt in which an elastic layer and a mold releasing layer are laminated on a substrate, and when the creep value $C_{HU}$ which is measured from the mold releasing layer side is defined by the following formula.

$$C_{HU} = (h_2 - h_1)/h_1 \times 100 \ (\%)$$

where $h_1$ is a pushed depth (mm) at the time of reaching to a test load which is kept in constant, and $h_2$ is a pushed depth (mm) when a predetermined period of time is lapsed after the test load is removed.

Because a flexibility of the fixing belt is caused mainly from a flexibility of the elastic layer, if the elastic layer has an appropriate flexibility, when the fixing belt is pressed by the fixing roller and the nip roller, the elastic layer is pressed and deformed to freely expand along a surface direction of the belt, thereby there is no specially constrained portion occurred on the material paper at the nipping portion, the occurrence of crumple on the material paper can be prevented.

According to this fact when the universal hardness test is achieved as described above if the creep value $C_{HU}$ is included within the range of $0.40 \leq C_{HU} \leq 3.50$ (%), the fixing belt can be evaluated as an acceptable product because it has appropriate flexibility (creep characteristic).

In this case the fixing belt can be judged as an acceptable product if a creep value $C_{HU}$ of the elastic layer is included within a range of $0.05 \leq C_{HU} \leq 0.80$ (%). In accordance with the present invention the fixing belt can be evaluated from a measured result when the elastic layer is formed on the substrate and a creep value $C_{HU}$ of the elastic layer is measured.

Also the fixing belt can be judged as an acceptable product if the creep value $C_{HU}$ of the mold releasing layer is included within a range of $3.0 \leq C_{HU} \leq 6.0$ (%). In accordance with the present invention the fixing belt can be evaluated from a measured result when the mold releasing layer is formed on the substrate and a creep value $C_{HU}$ of the elastic layer is measured.

In addition to the above described according to the present invention before the universal hardness test is achieved, a surface modification for the mold releasing layer is performed by UV ozone treatment, plasma treatment or EB (electron beam) treatment, or metal/metal oxide is coated in thin film on the mold releasing layer by vacuum deposition or sputtering. Consequently, in accordance with the present invention, the surface of the mold releasing layer is protected.

In accordance with the present invention the fixing belt which is loaded between a fixing roller and a heating roller to be used, and in which an elastic layer and a mold releasing layer are laminated on a substrate, is made such that a creep value $C_{HU'}$ is included within a range of $0.40 \leq C_{HU'} \leq 3.50$ (%) when the creep value $C_{HU'}$ which is measured from the mold releasing layer side is defined by a formula below.

$$C_{HU'} = (h_2 - h_1)/h_1 \times 100 \ (\%)$$

where $h_1$ is a pushed depth (mm) when a test load reaches a predetermined value which is kept for a predetermined period of time, and $h_2$ is a pushed depth (mm) when a predetermined period of time is elapsed after the test load is held.

By the above described structure because the elastic layer has an appropriate flexibility, when the fixing belt is pressed by the fixing roller and the nip roller, the elastic layer is pressed and deformed to freely expand along a surface direction of the belt, thereby there is no specially constrained portion occurred on the material paper at the nipping portion, the occurrence of crumple on the material paper can be prevented.

In the above described fixing belt, thickness of the substrate is made to become thinner from one side along an axial direction of the fixing roller to another side such that an outer periphery of the substrate has a tapered shape from one side along the axial direction of the fixing roller to another side.

At this point as one example, the substrate is made of a heat resistant material.

Further the elastic layer is laminated on an outer peripheral of the substrate, the mold releasing layer is laminated on the surface of elastic layer and a thickness of the elastic layer is made homogeneous from one side along the axial direction of the fixing roller to another side.

As for another example of the fixing belt in accordance with the present invention, the elastic layer is laminated on an outer peripheral of the substrate, the mold releasing layer is laminated on the surface of elastic layer and a thickness of the elastic layer is formed to become thicker from one side along the axial direction of the fixing roller to another side in order to cancel the tapered shape of the substrate.

According to the above described fixing belt when the fixing belt is loaded on the fixing roller to be used, because the fixing belt is urged to one side along an axial direction of the fixing roller a force which pulls the material paper to the one side along the width direction, is applied to the material paper while the material paper is fixed, thereby occurrence of crumple on the material paper during the fixing process can be prevented more effectively.

DETAILED DESCRIPTION OF THE PREFERRED EMBODIMENTS

Hereinafter, preferred embodiments of the present invention will be described with reference to the attached drawings.

Figure 1:
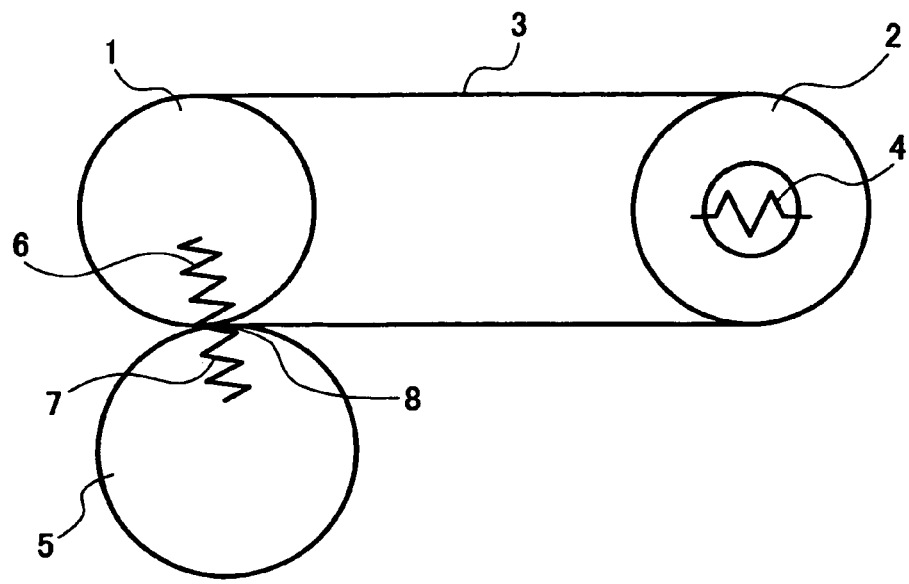
FIG. 1 is a schematic view showing a structure of the belt fixing device.

A belt-fixing device is schematically shown in FIG. 1. In the belt fixing device a fixing roller 1 and a heating roller 2 are parallely arranged and a fixing belt 3 according to the present invention which is formed into an endless like belt, for example, loaded between the fixing roller 1 and the heating roller 2 as shown in FIG. 1. A heater 4 is housed in the heating roller 2. A nip roller 5 is disposed under the fixing roller 1 to pinch the fixing belt 3.

The fixing roller 1 and the nip roller 5 are energized to thereby come closer each other by springs 6, 7 to pinch and press the fixing belt 3 from its both surfaces. By this arrangement, a nipping portion 8 is formed at a part where the fixing belt 3 and the nip roller 5 are contacted with each other. An image with toner is also fixed on a material paper when a paper which will be described in detail hereinafter is passed at the nipping portion 8.

Figure 2:
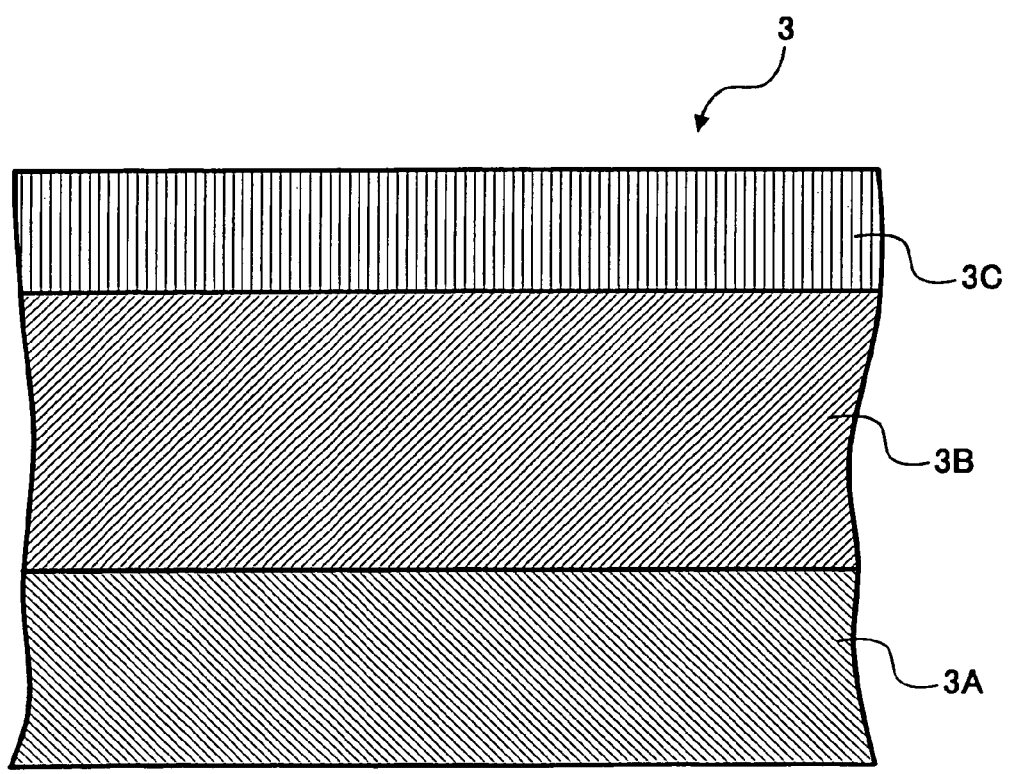
FIG. 2 is a cross sectional view showing a layered structure of the fixing belt.

The fixing belt 3 is composed of a substrate 3A, an elastic layer 3B which is laminated and formed on the substrate 3A, and a mold releasing layer 3C which is laminated and formed on the elastic layer 3B as shown in FIG. 2.

The substrate 3A is formed from a heat resistant material. As the heat resistant material, a metal such as stainless steel (SUS), nickel and the like, or heat resistant resin such as polyimide, polyamide-imide, fluorine contained resin and the like, can be used. When a metallic material is used, it is preferable that a thickness of the substrate 3A is less than 100 μm in consideration of a deflection of the fixing belt 3. When a heat resistant resin is used, it is preferable that the thickness of substrate 3A is included within a range of 30-200 μm in consideration of heat capacity (the thinner is the more advantageous from a view point of reduction in starting up time), strength (the thicker is the more advantageous) and further it is more preferable that it is approximately about 100 μm.

The elastic layer 3B is arranged in order to get a homogeneous image without uneven brightness, and surfaces of the belt are made flexible by this arrangement of elastic layer 3B. As for a materiel of the elastic layer 3B, silicon rubber, fluoro silicon rubber and the like can be used in consideration of a heat resisting property at a temperature for fixing process (less than 200 C.°). It is preferable that a thickness of the elastic layer 3B is approximately about 200 μm.

As for a material used for the mold releasing layer 3C, fluorochemical resin such as polytetrafluoroethylene resin (PTFE), tetrafluoroethylene—perfluoroalkylvinylether co-polymer resin (PFA), tetrafluoroethylene—propylene hexafluoride co-polymer resin (FEP) and the like, a mixture of these resin, or a compound in which these fluorochemical resin are dispersed in heat resistant resin, can be listed.

It is preferable that a thickness of the mold releasing layer 3C is approximately about 20 μm.

When in a case the elastic layer 3B is covered with the mold releasing layer 3C, toner releasing property and prevention of a paper powder fixing can be attained in preferable level without using silicon oil and the like (oil free device). However, because these resin which has mold releasing property generally has not elasticity such as rubber material, there is a possibility that uneven brightness problem occurs when the mold releasing layer 3C is thickly formed on the elastic layer 3B.

In other words, in order to attain at the same time a prevention of the uneven brightness and a maintaining of the mold releasing property for toner and paper powder, the mold releasing layer 3C must be formed such that flexibility of the elastic layer 3B is not eliminated. For this purpose it is necessary that a material of the mold releasing layer 3C is as flexible enough as possible and a thickness of it is as thin as possible.

As one of problem in the fixing belt 3 which is composed of the substrate 3A, elastic layer 3B and mold releasing layer 3C, it is noted to moderate a surface state and to form their properties as characteristic values. The fixing belt 3 is contacted with toner which is not fixed yet at its surface to give heat and pressure and to thereby fix the toner on the material paper. When toner is fixed on the material paper it is heated and pressed between fixing belt 3 and the nip roller 5, presence or absence of the occurrence of crumple is subtly influenced by a creep characteristic of the fixing belt 3 at its surface side. In other words the occurrence of crumple does not occur even when the material paper is expanded by application of heat and the expansion is absorbed adequately in a difference of creep characteristic at surface side of the fixing belt 3, but, in a case when the expansion is not absorbed, the occurrence of crumple happens.

In this situation, the inventors of present invention have found out that the occurrence of crumple can be predicted and prevented when the creep characteristic at surface side of the fixing belt 3 is evaluated whether a result of it is included within a predetermined range. As for a measuring method of the creep characteristic, Deutsche Institute fur Normung e.V. (German Institute for Standard) DIN 50359-1 is adopted.

Figure 3:
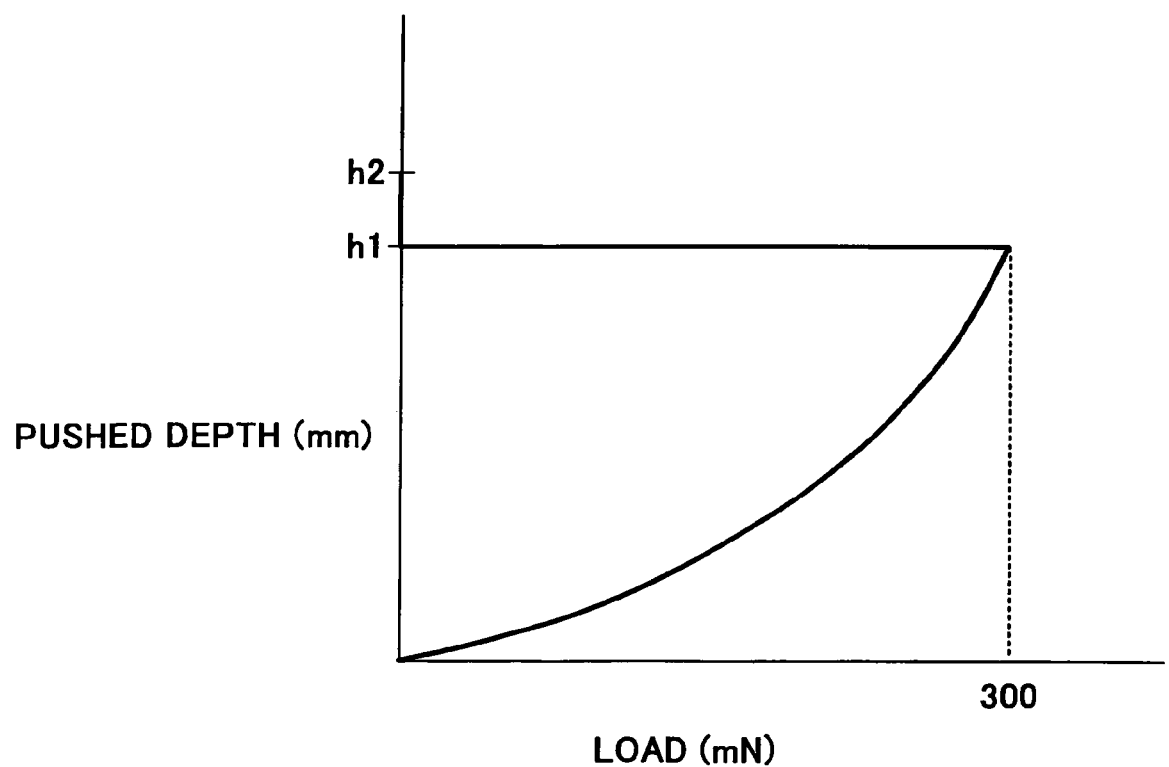
FIG. 3 is a graph showing a relationship between a load and a pushed depth when a universal hardness test is achieved.

In a universal hardness test a test bit with normal pyramid shape made of diamond is inserted in a test piece from its surface by applying a load (it is also referred to as a test load) and it is held for a predetermined time period $t_1$ when the load reaches a predetermined level (300 mN) to get a pushed depth $h_1$ at the moment as shown in FIG. 3, then $h_1$ is compared with another pushed depth $h_2$ of a value when the test bit is held for a predetermined time period $t_2$ without the test load to get the creep characteristic.

In this embodiment the pushed depth $h_1$ and $h_2$ are found out by the universal hardness test performed from the mold releasing layer 3C side for fixing belt 3 composed of substrate 3A, elastic layer 3B and mold releasing layer 3C, to thereby calculate the creep value $C_{HU}$ utilizing a formula below described.

$$C_{HU}=(h_2-h_1)/h_1 \times 100 \ (\%)$$

And when the calculated creep value $C_{HU}$ is included within a range below described, the fixing belt 3 can be judged as an acceptable product.

$$0.40 \leq C_{HU} \leq 3.50 \ (\%)$$

In other words the acceptable fixing belt 3 in this embodiment has a creep value $C_{HU}$ within the range of $0.40 \leq C_{HU} \leq 3.50$ (%) calculated when the fixing belt 3 is composed of the substrate 3A, elastic layer 3B and mold releasing layer 3C and it is measured from the mold releasing layer 3C side by the universal hardness test.

As described above when the creep value $C_{HU}$ which is measured from the mold releasing layer 3C side by the universal hardness test is included within the range of $0.40 \leq C_{HU} \leq 3.50$ (%), the fixing belt 3 is judged that the surface of it has appropriate flexibility at and especially it can be said that the elastic layer 3B has the optimum flexibility (creep characteristic). As described above if the elastic layer 3B has the optimum flexibility, the elastic layer 3B is pressed and deformed to freely expand along a surface direction of the belt when the fixing belt 3 is pressed by the fixing roller 1 and the nip roller 5 at the nipping portion 8, thereby there is no specially constrained portion occurred on the material paper at the nipping portion 8, the occurrence of crumple on the material paper can be prevented.

Hereinafter further embodiments of the present invention will be described in further detail.

Embodiment 1

At first a plurality kind of triple layer fixing belt 3 which is composed of the substrate 3A, the elastic layer 3B and the mold releasing layer 3C, are prepared and creep values of the respective fixing belt 3 are measured and then an experiment whether or not an occurrence of crumple does occur on a paper is performed with loading the respective fixing belt 3 on a belt fixing device as well.

For example as one example of the fixing belt 3 a substrate 3A which is made of poly-imide resin and it has dimensions of 60 mm diameter, 315 mm length and 50 μm thickness, is prepared, and a silicon rubber (hardness 25 degree by JIS: Japanese Industrial Standard K 6301) layer having 200 μm thickness is formed as the elastic layer 3B on the substrate 3A, and FEP resin layer having 8 μm thickness is further formed as the mold releasing layer 3C on the elastic layer 3B and a test piece of the fixing belt is made. The creep value at the surface of this fixing belt 3 is examined and the value is calculated as 1.38 (%).

As another example of the fixing belt 3 a substrate 3A which is made of poly-imide resin and it has a dimension of 60 mm diameter, 315 mm length and 100 μm thickness, is prepared, and a silicon rubber layer having 50 μm thickness is formed as the elastic layer 3B on the substrate 3A, and FEP resin layer having 3 μm thickness is further formed as the mold releasing layer 3C on the elastic layer 3B and a test piece of the fixing belt is made. The creep value at the surface of this fixing belt 3 is examined and the value is calculated as 0.35 (%).

As for the substrate 3A several kinds of test pieces which are made of stainless seamless belt (thickness 30 μm, 40 μm, 60 μm), Ni seamless belt (thickness 30 μm, 40 μm, 60 μm), polyimide seamless belt (thickness 30 μm, 50 μm, 100 μm, 200 μm), polyamideimide seamless belt (thickness 50 μm, 100 μm, 200 μm), and fixing belt with seam made of the above described materials are prepared.

As for the elastic layer 3B several kinds of test pieces which are made of fluoroic rubber are prepared as well as the silicon rubber. Test pieces of the elastic layer 3B are prepared with thickness of 50 μm, 100 μm, 150 μm, 200 μm, 400 μm, and 500 μm, which are made of materials having hardness (JIS K 6301) 5 degree, 15 degree, 25 degree, 35 degree and 45 degree.

As for the mold releasing layer 3C several test pieces which are made of resins such as PTFE, PFA, FEP and ETFE are prepared with their thickness of 3 μm, 10 μm, 20 μm and 50 μm.

A priming coat is achieved between the respective layers of the fixing belt 3 according to its necessity.

As for measuring condition, the test load is set at 300 mN, the holding time $t_1$ at pushed depth $h_1$ is set at 5 seconds, and the holding time $t_2$ which is a time till the pushed depth becomes $h_2$ after the test load has been taken off, is set at 10 seconds as well. As for a measuring machine, Super Micro Hardness Tester H-100 made by Fischer Instrument Corporation is used.

At this point because the fixing belt 3 is not so stiff, the measurement of creep value and the like is performed after a specimen is cut in a sheet shape and it is adhered on BK7 glass surface and harden for a strength compensation.

Figure 4:
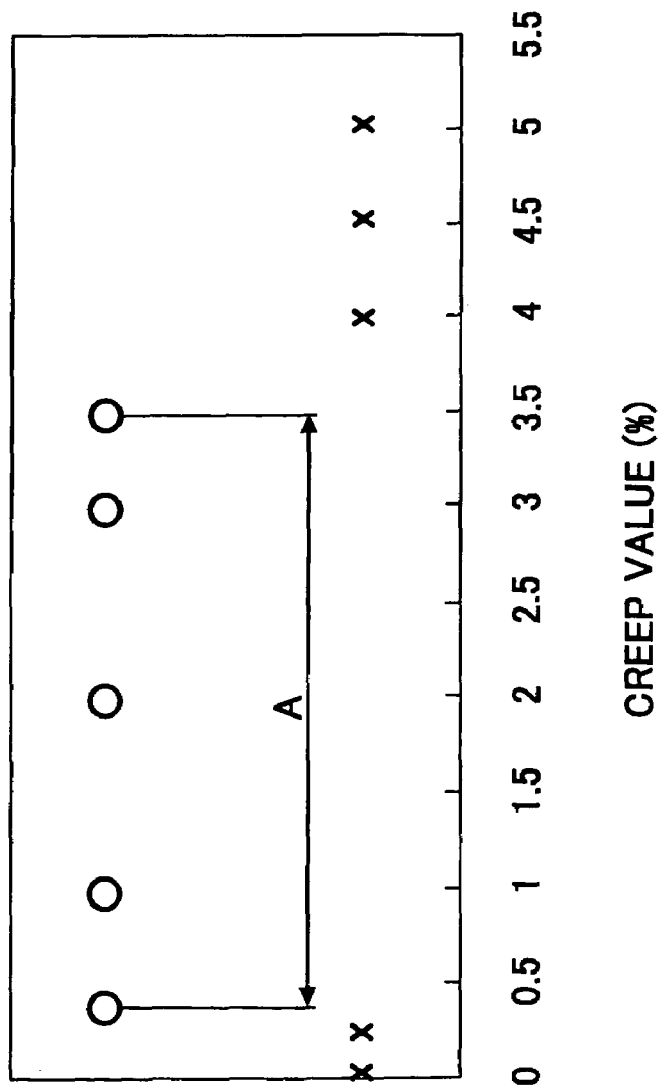
FIG. 4 is a graph showing a relationship between a creep value of the fixing belt with three layers and an occurrence of crumple in a material paper.

About the respective specimen of fixing belt 3 which are prepared as above described, it is observed whether an occurrence of crumple on the material paper occurs or not, and the result of observation are compiled to thereby find out a tendency of relationship between the creep values and the occurrences of crumples as shown in FIG. 4.

Judging from FIG. 4, it is found out that there is no occurrence of crumple on the material paper when the creep value $C_{HU}$ is included within a range A which is defined by a formula $0.40 \leq C_{HU} \leq 3.50$ (%).

Embodiment 2

Secondly a creep value of the elastic layer 3B is measured to thereby observe a relation between the value and the occurrence of crumple about the elastic layer 3B which is formed on the substrate 3A as well. At this point the substrate s 3A and the elastic layers 3B are quite the same as prepared for the Embodiment 1 as described above.

Figure 5:
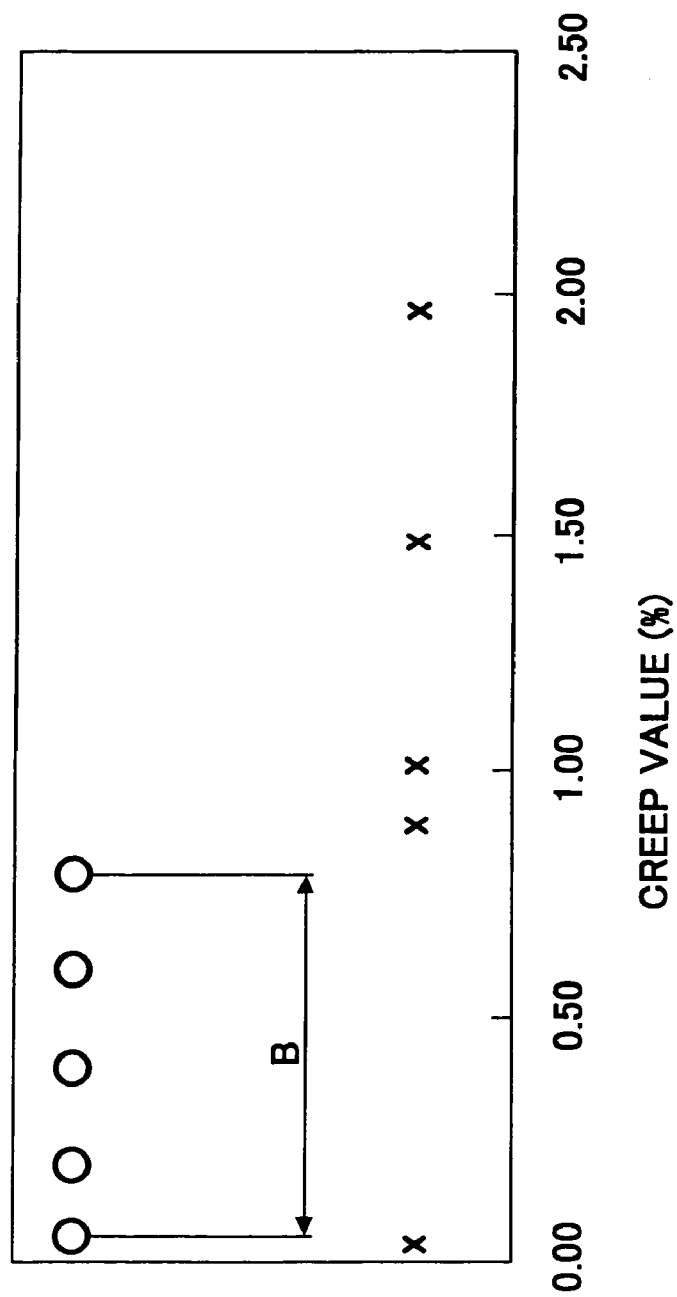
FIG. 5 is a graph showing a relationship between the creep value of an elastic layer and the occurrence of crumple in a material paper.

As a result when they are compiled, it is found out that there is a tendency as shown in FIG. 5 between the creep values and the occurrences of crumples.

Judging from FIG. 5 it is found out that there is no occurrence of crumple on the material paper when the creep value $C_{HU}$ of the elastic layer 3B is included within a range B which is defined by a formula $0.05 \leq C_{HU} \leq 0.80$ (%).

Embodiment 3

Thirdly a creep value of the mold releasing layer 3C is measured to thereby observe a relation between the creep value and the occurrence of crumple on the material paper about the mold releasing layer 3C which is formed on the substrate 3A as well. At this point the substrate s 3A and the mold releasing layers 3C are quite the same as prepared for the Embodiment 1 as described above.

Figure 6:
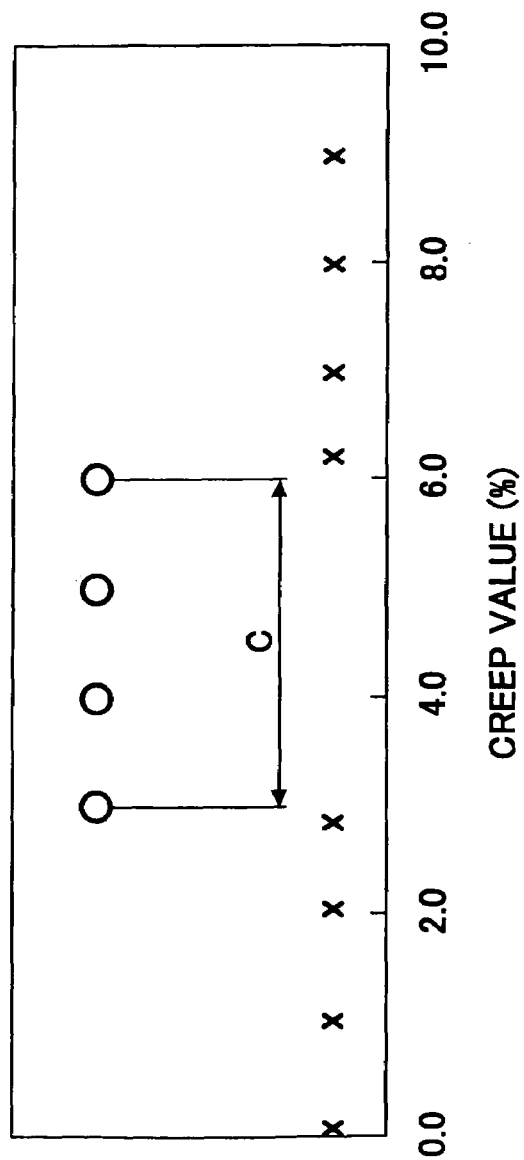
FIG. 6 is a graph showing a relationship between the creep value of a mold releasing layer and the occurrence of crumple in a material paper.

As a result when they are compiled it is found out that there is a tendency as shown in FIG. 6 between the creep values and the occurrence of crumple.

Judging from FIG. 6 it is found out that there is no occurrence of crumple on the material paper when the creep value $C_{HU}$ of the mold releasing layer 3C is made within a range C which is defined by a formula $3.0 \leq C_{HU} \leq 6.0$ (%).

Embodiment 4

Next, the fixing belts 3 in which a surface modification layer or thin film is coated on the mold releasing layer 3C, are formed and the creep values of them are measured to thereby observe a relation between the creep value and the occurrence of crumple on the material paper in the same manner as the Embodiment 1.

As for the surface modification method UV (ultraviolet) ozone treatment, plasma treatment and EB (electron beam) treatment are performed, and the thin film is coated by vacuum deposition method or sputtering method. As for material of thin film coating, metal such as aluminum, silver, gold, chromium and the like and metal oxide such as $Al_2O_3$ and the like are selected and coated.

As an example of UV ozone treatment, a low voltage mercury vapor lamp SUV-90S which is made by Sen Engineering Corp. is used as a light source and the samples are irradiated for 5 minutes with a distance of 50 mm and prepared as specimens. As for the substrate of treated specimen the poly-imide resin which is described in the Embodiment 1 is formed to have dimensions of 60 mm diameter, 315 mm length and 50 μm thickness. And the silicon rubber (hardness; 25 degree (JIS K 6301)) is formed on the substrate with a thickness of 200 μm and further FEP resin is formed on the silicon rubber with a thickness of 8 μm.

Also by this embodiment it is found out that there is no occurrence of crumple on the material paper when the creep value $C_{HU}$ is made within the range which is defined by the formula $0.40 \leq C_{HU} \leq 3.50$ (%).

Embodiment 5

Next, to analyze a relation between the creep value and the occurrence of crumple on a fixing belt 3 which has varieties of layers composition, two kinds of single layer specimens which are composed only of the substrate 3A and one mold releasing layer 3C (single layer 1 and single layer 2), one kind of double layer specimen which is composed of the substrate 3A and the elastic layer 3B (double layer 1), and five kinds of triple layer specimens which are composed of the substrate 3A, the elastic layer 3B and the mold releasing layer 3C (triple layer 1, triple layer 2, triple layer 3, triple layer 4 and triple layer 5) are selected and prepared.

And the universal hardness test is performed on the above described single layer specimen, double layer specimen and triple layer specimen in the same manner as described in the Embodiment 1 to measure the creep values of the respective specimens.

The measured results are listed below. At this point in the list, unit (%) for the resulted creep values are omitted.

(Measurement Result for Single Layer Specimens)
Single layer specimens 1: 4.33, 3.82, 3.94, 3.69
Single layer specimens 2: 4.26, 3.87, 4.23, 4.23, 4.32, 4.96, 4.67, 4.40 3.57, 3.62, 4.30, 4.30, 4.39, 4.45, 4.40, 4.40 4.29, 3.98, 4.59, 3.76, 4.68, 4.37
(Measurement Result for Double Layer Specimens)
Double layer specimens 1: 0.30, 0.39, 0.33
(Measurement Result for Triple Layer Specimens)
Triple layer specimens 1: 1.12, 0.70, 1.61, 0.80, 0.66, 0.69 0.94, 0.77, 1.38, 1.33, 1.00, 1.06 2.01, 0.93, 1.08, 0.80, 1.20, 3.13
Triple layer specimens 2: 1.049, 1.012
Triple layer specimens 3: 0.42, 0.44, 0.49, 0.52, 0.56 0.59, 0.47, 0.61, 0.59
Triple layer specimens 4: 0.883, 0.758, 1.06, 0.839, 0.87, 0.934
Triple layer specimens 5: 1.77, 1.75, 1.74, 2.28, 3.16
When the measured results are put in order, a table below described is obtained.

TABLE 1

|  | Maximum Value | unit (%) Minimum Value |
|---|---|---|
| Single layer specimen | 4.96 | 3.57 |
| Double layer specimen | 0.39 | 0.30 |
| Triple layer specimen | 3.16 | 0.42 |

Figure 7:
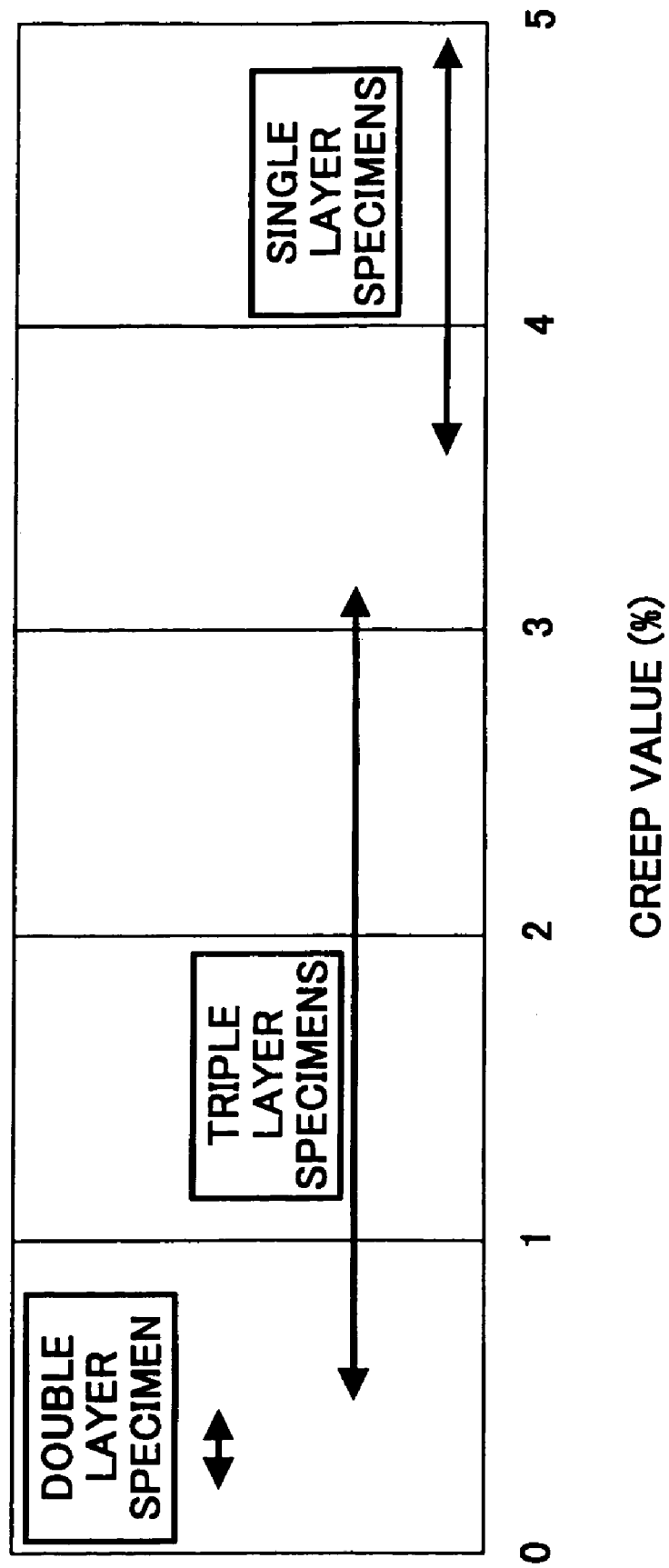
FIG. 7 is a graph showing a distribution state of the creep values for a single layer specimen, a double layer specimen and a triple layer specimen.

When a content of table 1 is depicted in a schematic diagram, the result is obtained as FIG. 7. The creep values for the triple layer specimens locate between those of double layer specimens and single layer specimens and no overlapping is observed among the creep values for double layer specimens and single layer specimens. By this result it is found out that the creep values for the triple layer specimen can be estimated without any performing measurement intentionally when the creep values for double layer specimen and single layer specimen are measured and a range of distribution for the values can be fixed.

Embodiment 6

Figure 8:
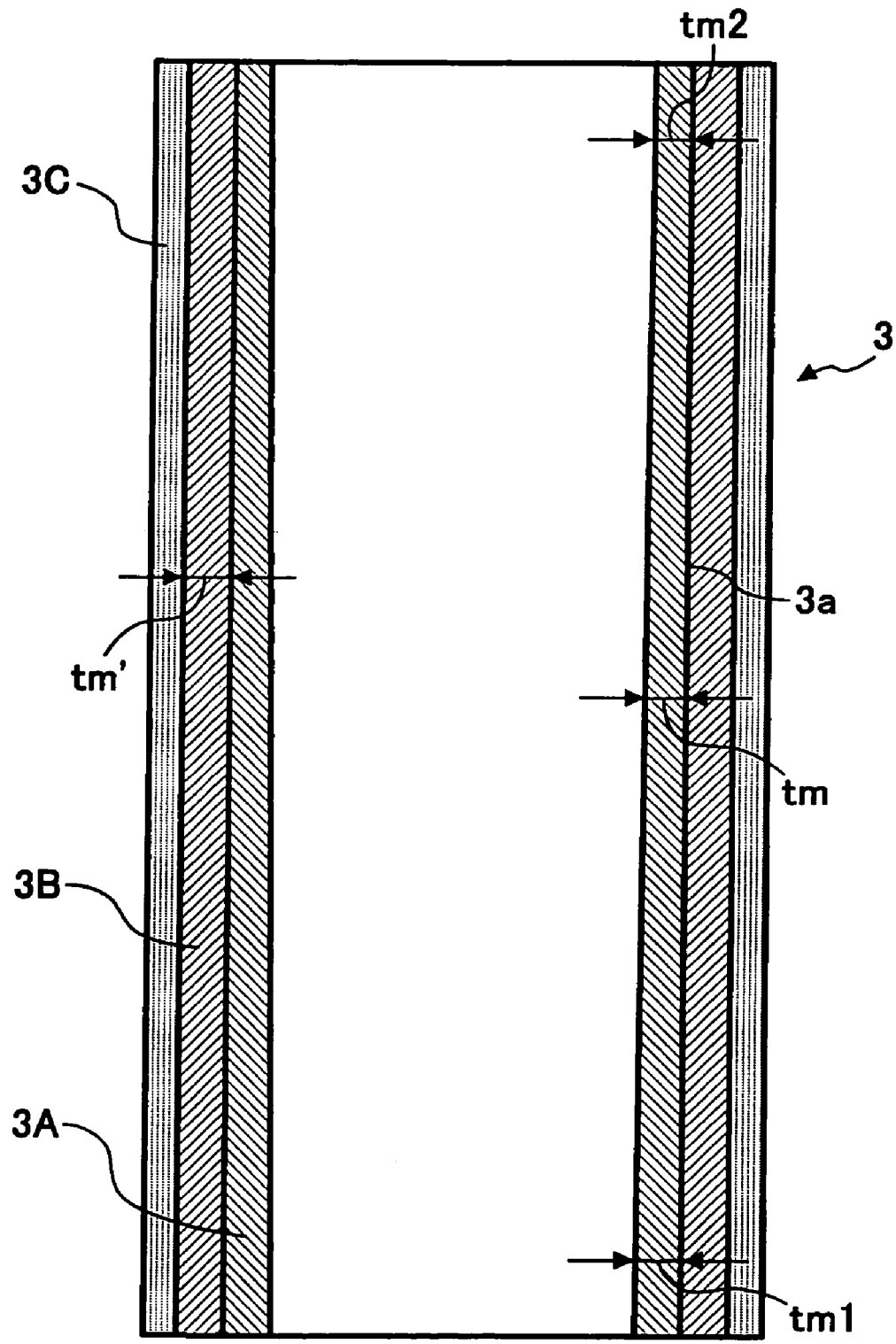
FIG. 8 is a diagram showing a cross sectional view of the fixing belt in which a tapered structure is given on outer peripheral surface of a substrate of the fixing belt from one side along axial direction of the fixing roller to another side.

In this embodiment the substrate 3A is formed in a manner that layer thickness t of the substrate 3A is made to become thinner from one side along the axial direction of the fixing roller 1 to another side such that a surface 3a of the outer periphery of substrate 3A has a tapered shape from one side along the axial direction of the fixing roller 1 to another side as shown in FIG. 8.

The layer thickness tm are made as that $tm_1$ at one side along the axial direction is, for example, 105 μm and $tm_2$ at another side along the axial direction is, for example, 95 μm and an average thickness tm is, for example, 100 μm.

Figure 9:
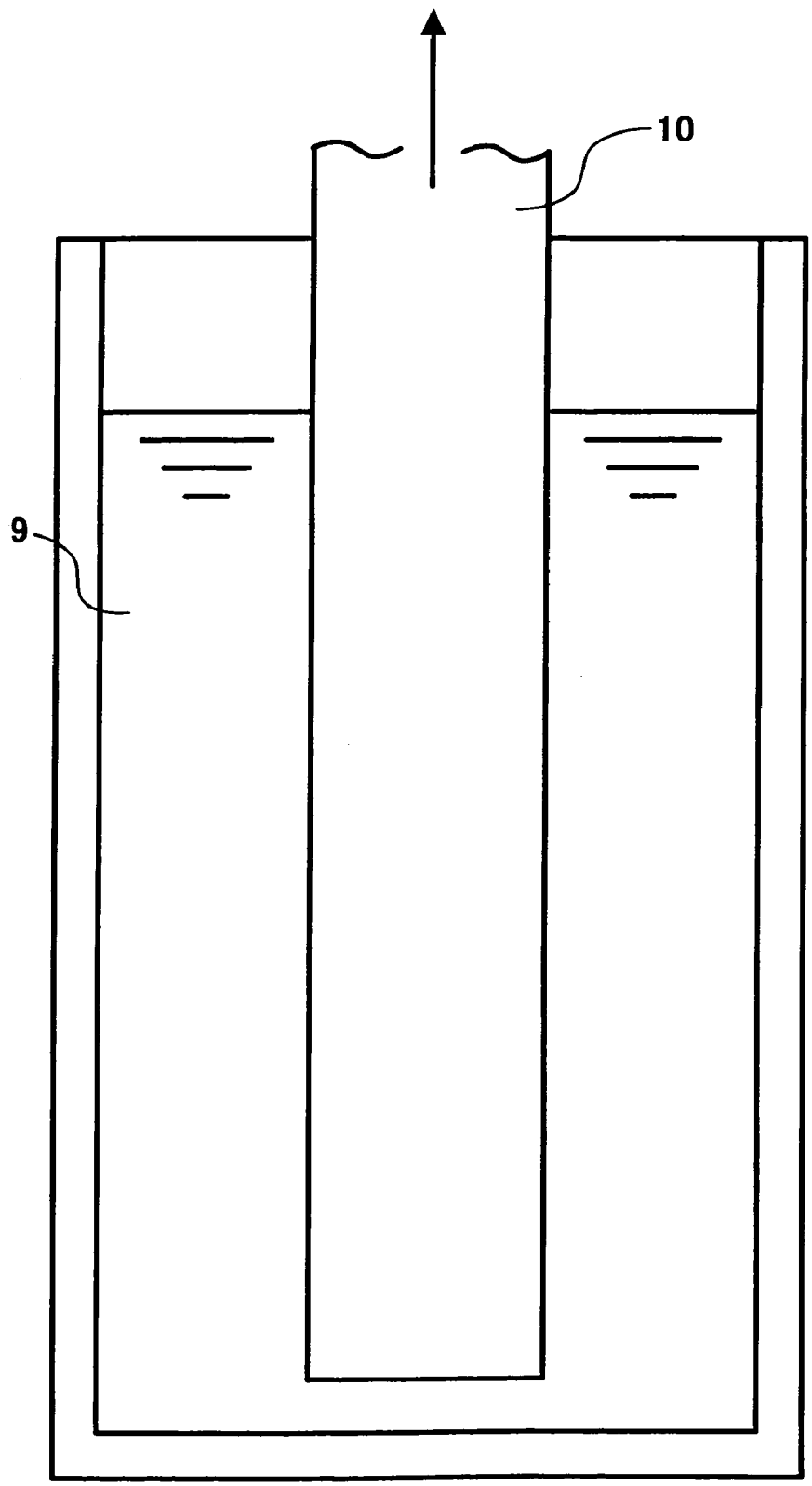
FIG. 9 is an explanatory diagram showing one example of a manufacturing method of the substrate in the fixing belt shown in FIG. 8.

When in a case the substrate 3A is formed of, for example, polyimide resin as a heat resistant material, a dipping method is adopted and a cylinder shaped arbor 10 is dipped into a polyimide resin solution 9 as shown in FIG. 9. Further, a withdrawing speed of the cylinder shaped arbor 10 is controlled when the cylinder shaped arbor 10 is pulled up with the polyimide resin solution 9 to be attached around the surface, thereby the attachment amount of poly-imide resin around the cylinder shaped arbor 10 is controlled and the substrate 3A is obtained in which a surface 3a of the outer periphery of substrate 3A has a tapered shape from one side along the axial direction of the fixing roller 1 to another side.

The elastic layer 3B is formed in the same manner on the surface 3a of outer periphery of the substrate 3A which is formed as described above, and the mold releasing layer 3C is formed on the elastic layer 3B, but at this point the layer thickness tm' of the elastic layer 3B is made to become homogeneous from one side along the axial direction to another side.

Figure 10:
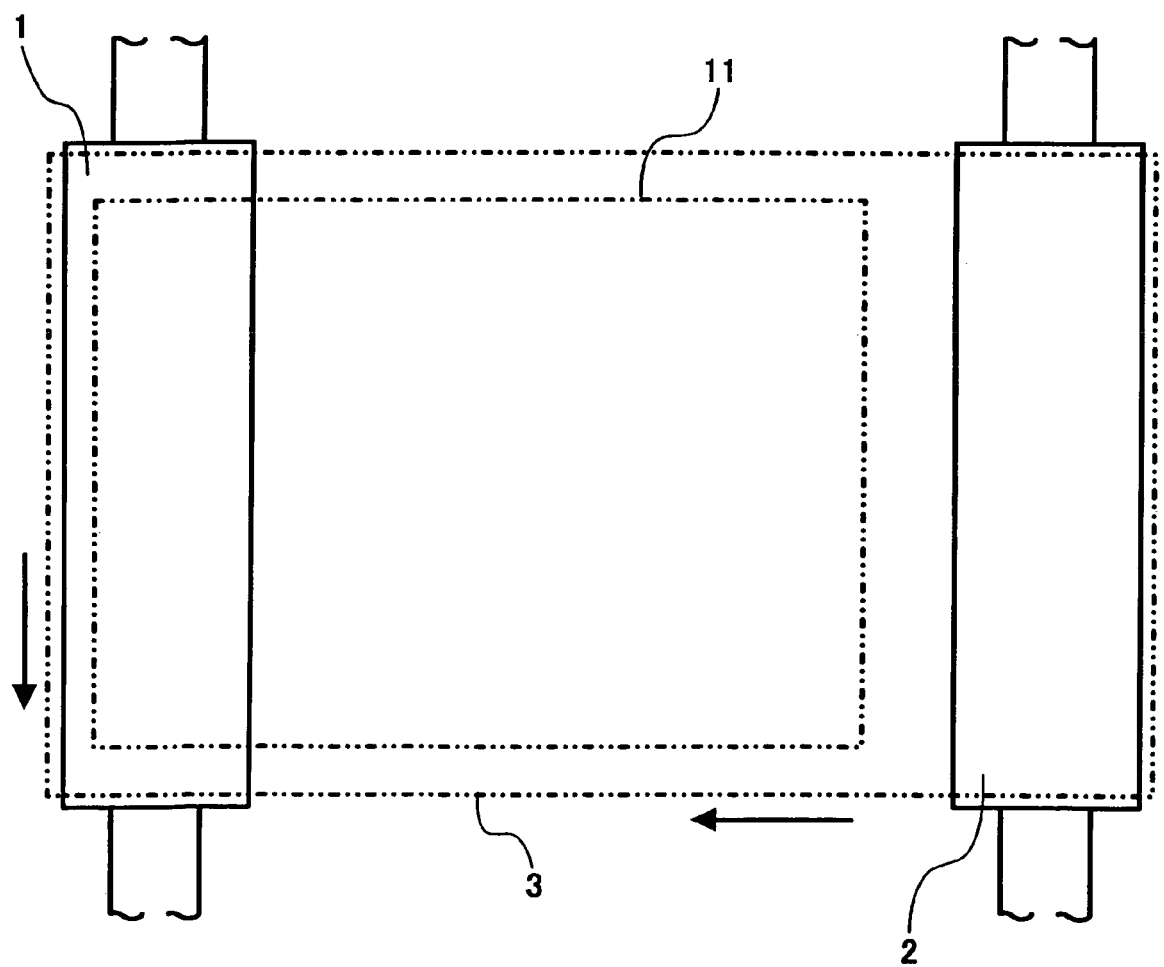
FIG. 10 is an explanatory diagram showing a reason why a force which urges the fixing belt to one side along axial direction of the fixing roller, is generated when the fixing belt shown in FIG. 8 is loaded between the fixing roller and a heating roller.

By utilizing the fixing belt 3 which is formed as described above, when the fixing belt 3 is loaded as shown in FIG. 10 between the fixing roller 1 and the heating roller 2 to use, because a pressing force of the fixing roller 1 and the nip roller 5 onto the fixing roller 3 is divided by a tapered structure (slope) of the substrate 3A into a component force which urges the fixing belt 3 to one side along the axial direction (direction shown by an arrow $P_2$ in FIG. 10) of the fixing roller 1 and a nipping component force which nips the fixing belt 3, while the fixing belt 3 is driven and rotated by a rotation of the fixing roller 2 in a direction shown by an arrow $P_1$, a force which pulls the material paper 11 to the one side along the width direction, is applied to the material paper 11, and then the pulling force for the material paper 11 to the one side direction is made possible to be continued applying while the toner on the material paper is fixed, thereby occurrence of crumple on the material paper 11 during the fixing process can be prevented more effectively.

Figure 11:
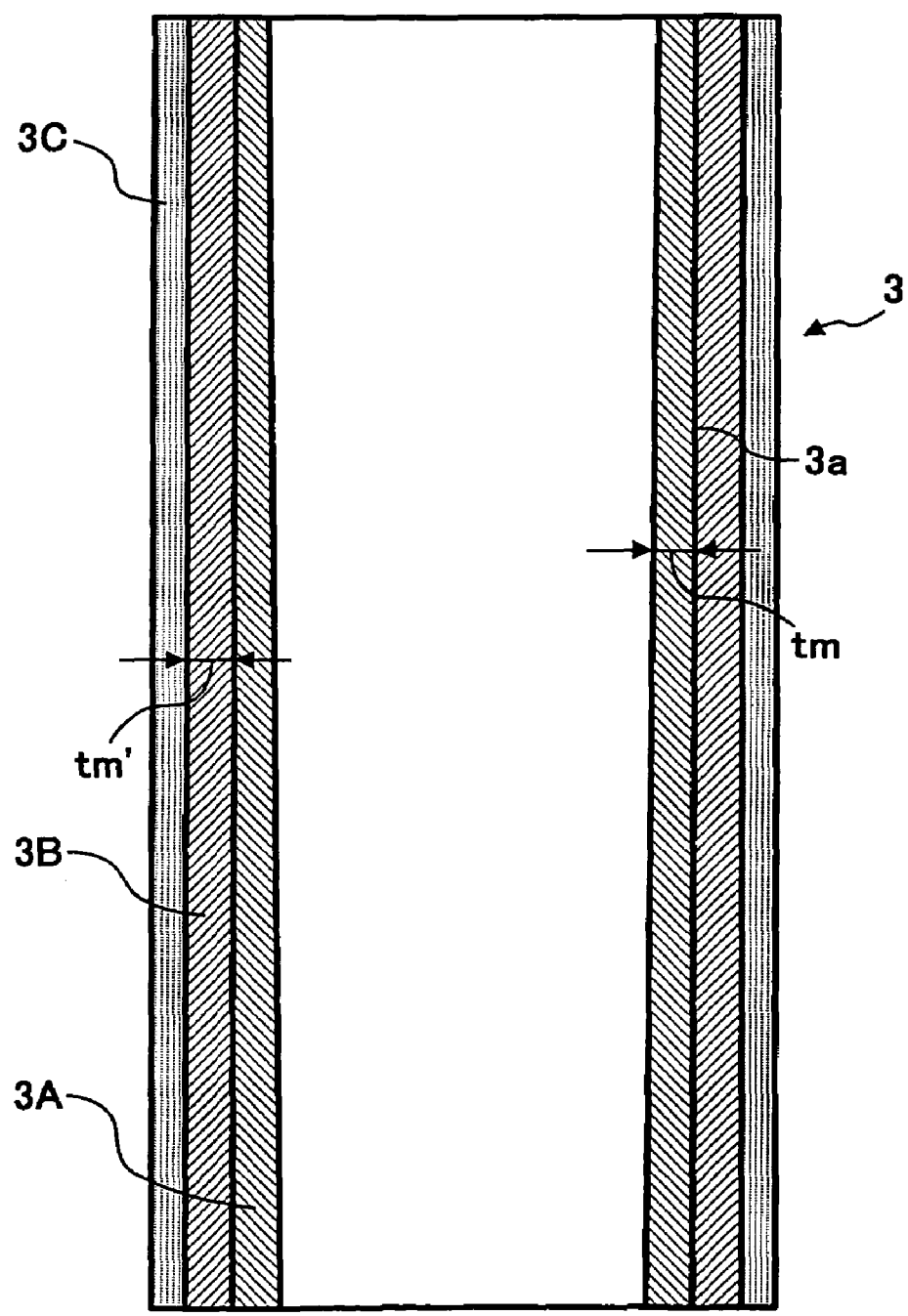
FIG. 11 is a cross sectional view showing one modification example of the fixing belt shown in FIG. 8.

In this embodiment 6 a structure is employed in which the surface of elastic layer 3B has also tapered shape along the axial direction, however, another structure is also recommendable in which the thickness tm' of elastic layer 3B is made to become thicker from one side along the axial direction to another side as shown in FIG. 11 such that a surface 3b of outer periphery of the elastic layer 3B cancels the tapered shape of the substrate 3A.

Also in this case because the outer shape of fixing belt 3 while it is driven to rotate, is defined by the outer shape of substrate 3A which is hard in stiffness, it is made possible to apply a pulling force in a constant direction to the material paper while it is fixed, thereby occurrence of crumple on the material paper 11 can be prevented more effectively.

EFFECT OF THE INVENTION

As described above in accordance with the present invention the occurrence of crumple on the material paper can be prevented by mean of accurately evaluating whether the fixing belt has a appropriate flexibility on the surface or not.

The fixing belt can be evaluated by means of creep value of the elastic layer.

The fixing belt can be also evaluated by means of creep value of the mold releasing layer.

Further in accordance with the present invention the fixing belt is provided by which the surface of mold releasing layer can be protected and the occurrence of crumple on the material paper can be prevented.

Especially the occurrence of crumple can be prevented more effectively because the pulling force is made possible to apply from one side along the axial direction to another side to the material paper while the fixing roller is driven to rotate.

The invention claimed is:
1. A method for evaluating a fixing belt, comprising:
    forming a fixing belt which includes a substrate, an elastic layer laminated on the substrate and a mold releasing layer laminated on the elastic layer;

performing a universal hardness test for said fixing belt; and judging as an acceptable product if a creep value $C_{HU}$ is included within a range of $0.04 \leq C_{HU} \leq 3.50 (\%)$ when said universal hardness test is performed for said fixing belt and when said creep value $C_{HU}$ which is measured from the side of said mold releasing layer is defined by a formula below $$C_{HU}=(h_2-h_1)/h_1 \times 100(\%)$$

where $h_1$ is a pushed depth when a test load reaches a predetermined value which is kept for a predetermined period of time, and $h_2$ is a pushed depth when a predetermined period of time is elapsed after the test load is removed.

2. The evaluating method for a fixing belt as claimed in claim 1, wherein the judging as an acceptable product includes judging if the creep value $C_{HU}$ of said elastic layer is included within a range of $0.05 \leq C_{HU} \leq 0.80 (\%)$.

3. The evaluating method for a fixing belt as claimed in claim 1, wherein the judging as an acceptable product includes judging if the creep value $C_{HU}$ of said mold releasing layer is included within a range of $3.0 \leq C_{HU} \leq 6.0 (\%)$.

4. The evaluating method for a fixing belt as claimed in claim 1, wherein before said hardness test is performed, a surface modification for said mold releasing layer is performed by UV ozone treatment, plasma treatment or EB treatment, or metal/ metal oxide is coated in thin film on the surface of said mold releasing layer by vacuum deposition or sputtering.

* * * * *